United States Patent [19]

Skrabal

[11] Patent Number: 5,237,993
[45] Date of Patent: Aug. 24, 1993

[54] PROCESS AND DEVICE FOR DETERMINING PARAMETERS OF INTEREST IN LIVING ORGANISMS

[75] Inventor: Falko Skrabal, Graz, Austria
[73] Assignee: AVL Medical Instruments AG, Schaffhausen, Switzerland
[21] Appl. No.: 794,244
[22] Filed: Nov. 19, 1991

Related U.S. Application Data

[62] Division of Ser. No. 415,267, Aug. 2, 1989, Pat. No. 5,097,834.

[30] Foreign Application Priority Data

Feb. 2, 1987 [AT] Austria ............................. A 201/87
Jul. 9, 1987 [AT] Austria ............................. A 1732/87

[51] Int. Cl.⁵ ............................................. H61B 5/00
[52] U.S. Cl. .................................. 128/632; 128/637; 604/50
[58] Field of Search ..................... 128/632–635, 128/637, DIG. 13; 604/27, 28, 48–50

[56] References Cited

U.S. PATENT DOCUMENTS

| | | | |
|---|---|---|---|
| 4,221,567 | 9/1980 | Clark et al. | 128/635 |
| 4,240,438 | 12/1980 | Updike et al. | 128/635 |
| 4,253,456 | 3/1981 | Schindler et al. | 128/633 |
| 4,516,580 | 5/1985 | Polangi | 128/632 |
| 4,632,119 | 12/1986 | Reichstein | 128/632 |
| 4,633,878 | 1/1987 | Bombardieri | 128/635 |
| 4,761,371 | 8/1988 | Bell et al. | 435/68 |
| 4,774,955 | 10/1988 | Jones | 128/632 |
| 5,106,365 | 4/1992 | Hernandez | 128/632 |

FOREIGN PATENT DOCUMENTS

8101794 7/1981 World Int. Prop. O. .......... 128/632

Primary Examiner—Stephen C. Pellegrino
Assistant Examiner—Michael Rafa
Attorney, Agent, or Firm—Watson, Cole, Grindle & Watson

[57] ABSTRACT

In order to determine at least one parameter of interest in a living organism, a perfusion is directly introduced in the tissues. After its partial balancing by the tissue parameter of interest, the perfusion fluid is collected and analyzed for the parameter of interest, as well as for endogenous or exogenous marker properties indicative of the degree of interaction between the perfusion fluid and the tissue, in such a way that the parameters of interest can be determined with the help of such characteristic properties. Contrary to usual processes, used exclusively inside blood vessels or other body cavities filled with liquid, this process creates in the tissues, i.e. in the closed cellular structure, a previously inexistent cavity, in which the perfusion fluid introduced in the tissue interacts directly with the organic tissue, with no intervening membranes. The transfer of the measurement site into the tissue completely eliminates the risk of the thromboses and embolies, besides strongly reducing the risk of infection.

11 Claims, 9 Drawing Sheets

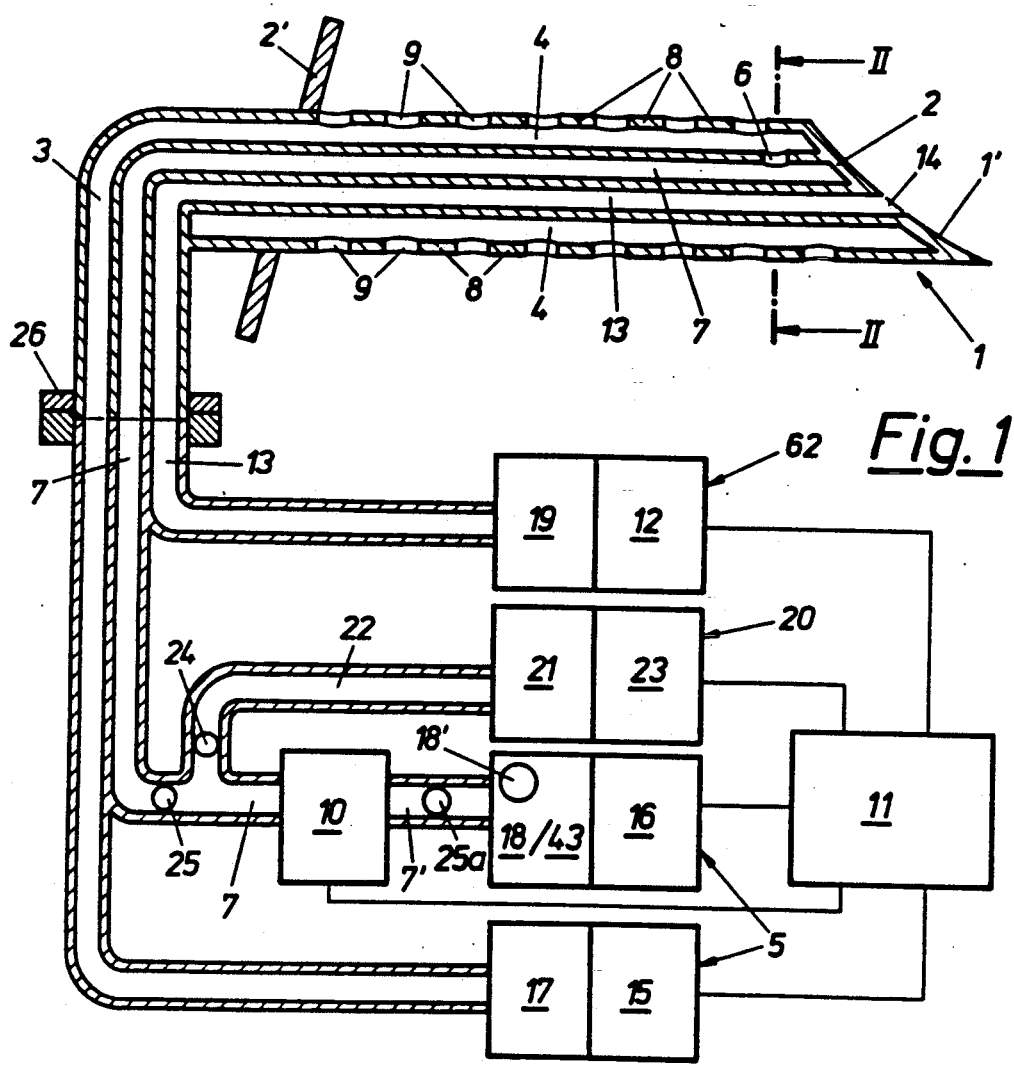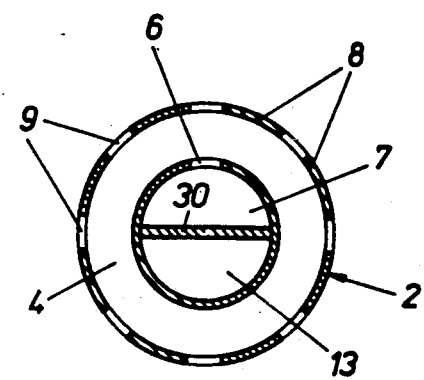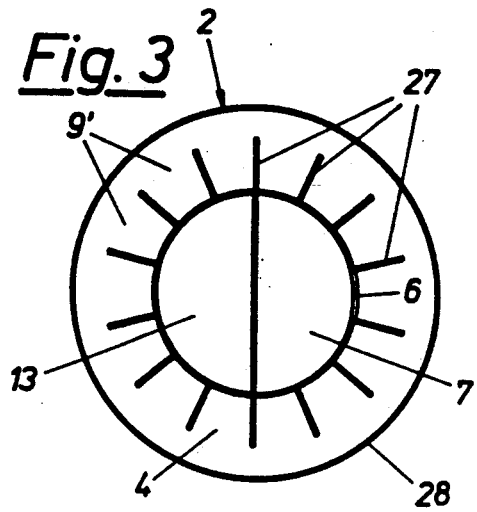

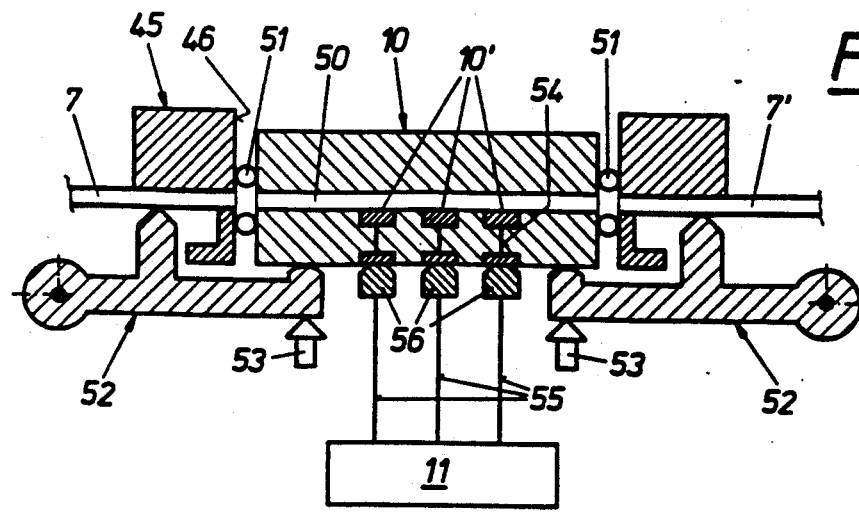
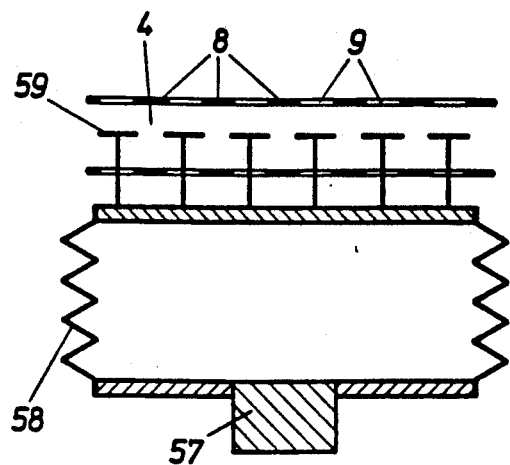
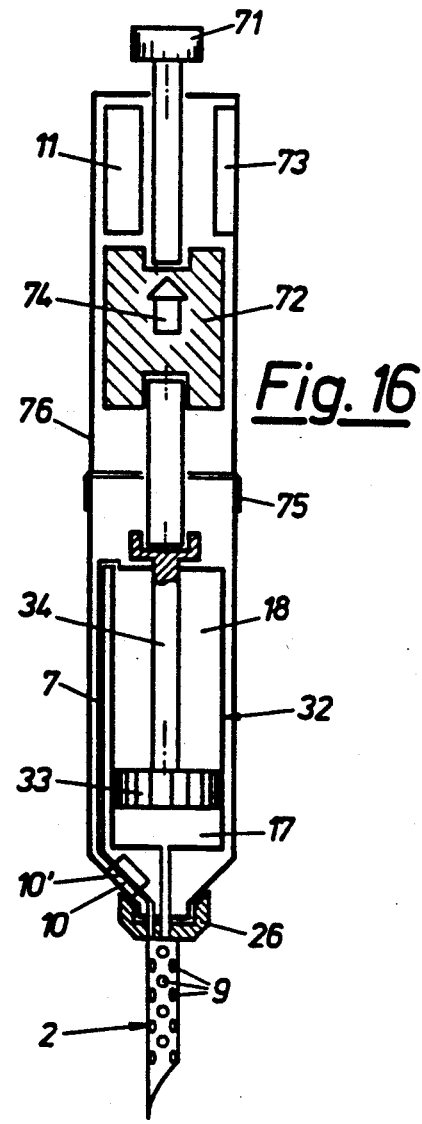

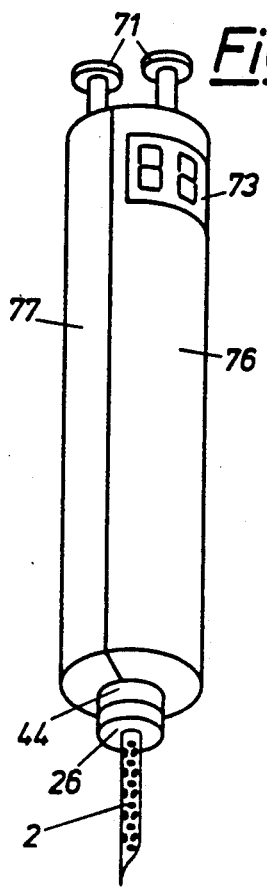
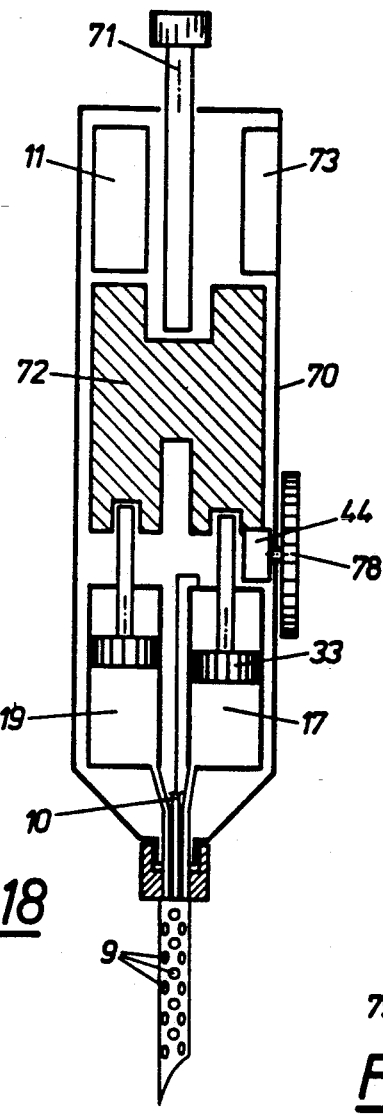
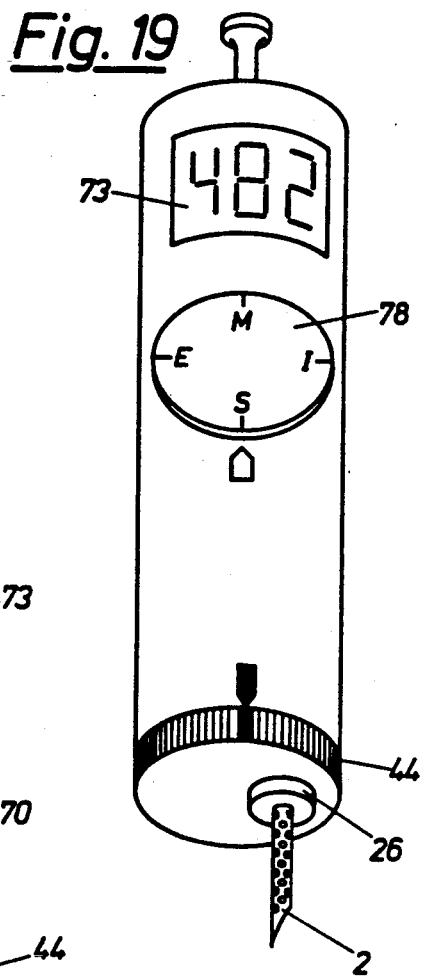
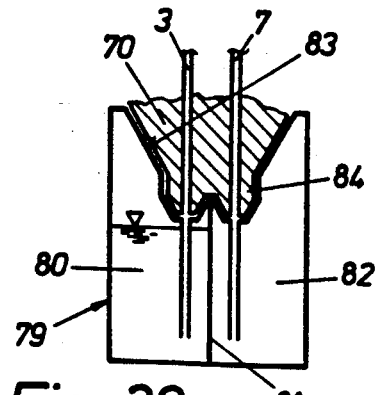

PROCESS AND DEVICE FOR DETERMINING PARAMETERS OF INTEREST IN LIVING ORGANISMS

CROSS REFERENCE TO RELATED APPLICATION

This application is a divisional of application Ser. No. 415,267, filed Aug. 2, 1988, now U.S. Pat. No. 5,097,834.

This invention relates to a process and device for determining parameters of interest in living organisms.

In medical applications it is often necessary to analyze the composition of body fluids repeatedly or continuously so as to be able to detect and eliminate disturbances of the homeostasis. In order to render frequent withdrawals of blood unnecessary, numerous attempts have been made over the past years to place sensors in the patient's body in order to obtain a steady flow of information. The use of sensors fastened to the surface of an esophagus catheter is described in EP-A 101 595, for example.

The disadvantage of sensors implanted in the human body is that they are covered by a layer of coagulation products or cells within a very short time, thus yielding inaccurate readings. Another drawback is that sensors introduced into the body usually cannot be recalibrated.

Continuous measurements are of particular importance for determination of glucose concentrations in the human organism. As there is no simple method of continuously registering glucose, a method of indirect measurement has been described in U.S. Pat. No. 4,403,984 in which the concentration of glucose is obtained by measuring two other parameters, for instance osmolarity and conductivity.

In U.S. Pat. Nos. 4,221,567, 4,253,456 and 4,516,580 methods and apparatus for dialysis are disclosed in which at least one cannula or catheter is introduced into the bloodstream. By means of dialytic membranes, a test fluid may be fully equilibrated with the blood and may then be tested for the substance of interest. The membranes, which are subject to the test fluid on one side and to the body fluid, e.g. blood, on the other side, and which must be sufficiently large to permit adequate equilibration, are soon contaminated or clogged by body substances, however, which will quickly impede the exchange of the substances of interest. As regards the foreign bodies introduced into the bloodstream, stream, such as cannulas or catheters, there is constant danger of infection, thrombosis or embolism. Besides, there are few blood vessels available for long-term therapy, which will soon become obstructed by clots, thus preventing further use of the method.

Because of the above problems, there is no satisfactory device or method at present which would be suitable for continuous monitoring and adequate correction of tissue glucose and other substances by non-hospitalized patients.

SUMMARY OF THE INVENTION

It is an object of the invention to propose a simple method which should also be suitable for use by the patient, and a compact and portable device, for determining concentrations of substances in the living organism without the danger of infections, thromboses and embolisms.

In the invention this object is achieved by introducing a perfusion fluid directly into the tissue, by collecting the perfusion fluid after its partial equilibration with the tissue substance to be analyzed, by testing it for the substance to be analyzed as well as for endogenous or exogenous marker variables indicating the degree of interaction between perfusion fluid and tissue, and by determining the concentration of the substance in the tissue by means of these marker variables. Unlike conventional methods where only blood vessels or other fluid-filled cavities of the body are made use of, the method described by the invention utilizes the tissue, i.e., a solid body of cells, where a new cavity is created, in which the perfusion fluid introduced into the tissue enters into direct interaction with the tissue of the organism, i.e, without any intermediary membranes.

The method of the invention necessitates only partial equilibration, as the perfusion fluid is tested both for the parameter of interest and for endogenous or exogenous marker variables indicating the degree of interaction between perfusion fluid and tissue. The advantages of the new method are obvious. By relocating the measurement site into the tissue, thromboses and embolisms are completely eliminated and the risk of infection is greatly reduced. Another advantage is that measurements are not limited to the small number of blood vessels usually available for such manipulations.

It is proposed by the invention that at least one parameter from the group of ionic concentration, conductivity, impedance, osmolarity and density be analyzed as an endogenous marker variable of the perfusion fluid, and that at least one substance to be detected by chemical or physical methods be added to the perfusion fluid for measurement of exogenous marker variables. In this way the degree of equilibration of the injected perfusion fluid may be calculated from the measured quantity and the original quantity of the marker variable, such that the actual concentration in the tissue of the substance to be analyzed may be determined from the measured concentration of the parameter of interest and from the degree of dilution of the perfusion fluid injected.

In a device conforming to the objectives of the invention, a part of the device configured as a subcutanceous needle or catheter can be inserted into the tissue of the organism, and needle/catheter being provided with an exchange channel with openings along its wall, and the unit for feeding in the perfusion fluid and draining it after its partial equilibration with the substance to be analyzed — preferably glucose — and with endogenous or exogenous marker variables that are relatively constant compared to the substance to be analyzed, is connected to the exchange channel, and an analyzing unit connected to the feeding/draining unit is provided for measuring the concentration of the substance and one marker variable, which analyzing unit is connected to the evaluation unit determining the concentration in the tissue of the substance to be analyzed upon partial equilibration. The needle of the device described by the invention, which is inserted in the patient's body, thus has a channel on its surface whose walls are formed — at least partly — by the tissue itself, which will permit direct contact between the perfusion fluid and the tissue, inducing partial equilibration and facilitating subsequent collection and analysis.

It is further provided by the invention that a calibrating unit be provided for calibrating the sensors in the analyzer, comprising a container for the calibrating solution and a valve-controlled connecting tube into the analyzer, a pump for the calibrating solution and, if required, a collecting vessel for the calibrating solution. Thus, the analyzing unit for analyzing the substance of interest and the marker variable may be calibrated at specific intervals of time by means of a calibrating medium.

Based on the value calculated by the evaluation unit of the device for the concentration of the substance to be analyzed, the doses of the drugs to be administered and the type and extent of the appropriate therapy may be precisely adjusted to the particular patient, even over prolonged periods of time.

It has proved to be of advantage to provide a drug delivery device comprising a reservoir, pump and feeding tube for the drug, an opening in the feeding tube permitting the drug to drain into the tissue. By means of this system a drug is applied, preferably automatically, in accordance with the concentration of the parameter of interest to be analyzed.

According to the invention the concentration of glucose as the parameter of interest and the endogenous sodium and/or chloride concentration as a marker variable may be determined along with the temperature of the perfusion fluid, if required. It will also be possible, of course, to determine the glucose concentration as parameter of interest and to use the conductivity and/or impedance of the perfusion fluid as a marker variable. If an exogenous marker variable is to be employed, however, the invention will also permit determination of the glucose concentration as the parameter of interest and the concentration of a dye added to the perfusion fluid as a marker variable. Suitable exogenous marker substances are all compatible substances that are not found in the body, or found only in small quantities, such as dyes, whose dilutions may be measured photometrically, inulin, chemical as well as radioactive substances. For example, the calculation of the actual content of tissue glucose — using tissue sodium as a marker, which is present at a constant concentration of 140 mmole/l — would require that the measured glucose concentration be multiplied by a factor of 10, if a concentration of 14 mmole/l $Na^+$ is measured in the recovered perfusion fluid.

If ionic concentration is used as a marker variable, it will be advantageous to use a low-glucose, low-ion solution of approximately isotonic character as a perfusion fluid.

There are a variety of uses for the device described by the invention. As mentioned before, an artificial pancreas may be devised for the control of diabetes mellitus, or a system for registering and eliminating other hormone disturbances, e.g, related to the calcium metabolism, growth hormone, sexual hormones, etc.

Since the substances in the calibrating solution may be maintained at concentrations corresponding to those to be expected for the substance of interest in the perfusion fluid, linearity of the analyzing unit in the range of interest may be ensured by a single-point calibration. If this should not suffice, a second calibration must be performed, for instance for determining the zero point.

In the instance of an artificial pancreas, for example, glucose and sodium chloride will be added to the calibrating solution, a suitable concentration being 5-40 mg/deciliter or 5-40 mmole/l. In addition, the zero point can be recalibrated in a simple manner, if the perfusion fluid does not contain any, or only a small amount of the substance to be analyzed and marker substances, and if it can be delivered to the analyzing unit intermittently, without tissue contact.

A further development of the invention provides that the subcutaneous needle/catheter have at least two passages, one of which should be configured as an exchange channel with openings in its wall, and the other one as a drainage passage for the perfusion fluid, which is connected with the exchange channel via one or more openings near the tip of the subcutaneous needle/catheter, a large part of the surface of the needle serving as an equilibration area. This device can easily be handled by the patient as the use of subcutaneous needles or catheters poses no danger of an air embolism or thrombosis.

Via the subcutaneous needle inserted into the body, which is in connection with the feeding and drainage passages of the rest of the device, perfusion fluid is released into the body and subsequently withdrawn by means of a pumping/suction unit, the tissue pressing against the exchange channel and the surface of the needle without being able to enter it. In this way a sufficiently large area is formed at the surface of the subcutaneous needle or catheter, which may be utilized for equilibrating the perfusion fluid with the surrounding tissue. In the analyzing unit connected with the drainage passage two or more sensors or measuring electrodes are provided, which will measure the parameter of interest as well as the marker variable.

If a part of the inventive device, e.g., a subcutaneous needle is inserted into the body, there may be a lesion of body cells, which may release enzymes and, as a consequence, lead to the decomposition of glucose, for example. For this reason it might be necessary to take steps in order to prevent a reaction of the parameter of interest, e.g, glycolysis, in the perfusion fluid. According to the invention a reactant could be added to the perfusion fluid. For example, 3-phosphoglycerate could be used, which reacts in the presence of the required 3-phosphoglycerate kinase enzyme to form 1-3-biphosphoglycerate, using up ATP during this process. As the above enzyme is released together with the glycolytic enzymes, glycolysis and errors in the measured glucose values may be prevented. The resulting 1-3-biphosphoglycerate is not critical since renewed formation of glucose is rendered impossible due to a lack of further enzymes for gluconeogenesis in the subcutis. By optimum choice of the concentration of 3-phosphoglycerate in the perfusion fluid, the reaction must be prevented from shifting towards glycolysis again due to the formation of 1-3-biphosphoglycerate. For this purpose a concentration of 3-phosphoglycerate in the range of 5-100 mmole/l is recommended.

In the instance of differing diffusion constants, care should be taken that the diffusion constants of one or more marker substances and of the substance to be analyzed are additionally entered into the calculation of the concentration of the substance to be analyzed.

In a particularly simple version of the invention the proposal is put forward that the subcutaneous needle/catheter consist of two cannulas of different diameters, one contained within the other, such that an exchange channel of essentially annular cross-section is formed between the two cannulas, the inner cannula extending almost as far as to the tip of the outer one. In this two-channel variant of the subcutaneous needle the inner cannula is alternatingly used for withdrawing the perfusion fluid and delivering the drug.

Of course the drug could be applied in some other manner, for example with the use of a second injection needle or by oral administration. Due to the small exterior diameters possible with such subcutaneous needles (0.5 mm), the patient will only suffer a minimum of pain with the device described by the invention. Further variants of two-channel subcutaneous needles or catheters according to the invention are discussed in detail in the description of the drawings.

If a separate channel is to be envisaged for delivering the drug, the invention provides that the drug feeder tube, the drainage tube and the exchange channel be configured as concentric cannulas, the innermost cannula serving as a feed passage for the drug, with an opening towards the tissue near the tip of the subcutaneous needle/catheter, and the outermost cannula having numerous openings distributed over as large an area of its surface as possible, and that the drainage passage have at least one opening into the exchange channel near the tip of the subcutaneous needle/catheter, and that the drainage passage and the exchange channel be closed off in the area of the tip, if necessary. Further variants of three-channel subcutaneous needles/catheters are discussed in the description of the drawings.

As regards the configuration of the areas where the perfusion fluid enters into contact with the tissue surrounding the exchange channel, there are various other possibilities. For example, the invention provides that the subcutaneous needle/catheter have an inner cannula comprising a drainage passage and, possible, a feeder passage for a drug, the surface of the cannula being provided with a number of septa arranged lengthwise or helically, which septa will form the exchange channel once the cannula has been inserted into the tissue, and that the drainage passage have at least one opening into the space between the septa for drainage of the perfusion fluid, In another configuration of the invention, the subcutaneous needle/catheter can be partly made of a flexible material and — for protection of the septa — be put in a hollow needle which may be removed after insertion in the tissue.

If a hollow needle is used for puncturing, the subcutaneous needle or catheter may be made of flexible material which does not irritate the tissue and is comparatively comfortable to carry. Besides, the elastic septa of a subcutaneous catheter may be folded in the hollow needle, reducing the diameter for the hollow needle to be inserted into the tissue, and may unfold within the tissue to form the exchange channel.

As a further convenience for the patient, a plug-in connection is provided at the base end of the subcutaneous needle/catheter, through which, because of its geometric configuration, the passages contained in the subcutaneous needle/catheter may be properly aligned with the passages in the remaining part of the device.

In order to produce a compact, portable device, a preferred variant provides that the pressure/suction pump of the unit for feeding and draining the perfusion fluid be configured as a plunger pump, the plunger chamber, which is closed off on both ends, forming a collecting vessel for the perfusion fluid, which is separated from the reservoir by the plunger, and the driving rod of the plunger pump being sealed against the exterior wall of the pump. The above configuration is not restricted to the perfusion fluid, but may also be applied to the calibrating solution, in which instance the reservoir and the collecting vessel for the calibrating solution may be combined into a compact pumping device by means of a plunger pump, such that only one plunger pump with a drive will be required instead of pressure and suction pumps. In this way a compact variant of the device of the invention would necessitate only one plunger pump each for the perfusion fluid, the calibrating solution and the drug.

In a compact, simple and robust variant of the device, all device components, including their energy supply, are located in an implantable housing, whose surface — or at least parts thereof — is configured as an exchange channel with partly open walls, and as a reservoir for the perfusion fluid, as well as a reservoir for a drug can be refilled transcutaneously via a septum. In the instance of an implantable device, for example, an implantable insulin pump, part of the surface of the device, or the entire surface, could be configured as a meandering exchange channel acting as a large equilibration area, with its openings into the tissue. Because of the low rates of perfusion, an implantable device need not contain a collecting vessel for the perfusion fluid, since the fluid could be discharged into the body and absorbed there after it has been analyzed. The same applies for the calibrating solution.

In view of the safety requirements for implantable devices, it is recommended that the parameter of interest and the marker variable be measured by at least two independent analyzers, which will give off alarm signals if the measured values do not match.

Even if an implantable device as described by the invention offers certain advantages, the variants only based on the insertion of a subcutaneous needle/catheter into the body tissue also have their positive aspects. Among others, optimum conditions may be maintained during the measurement process, for example with regard to temperature, which may be maintained constant or entered into the calculation, and the pH value of the perfusion fluid, pH=5.6 ensuring optimum immobilization of the glucose oxidase enzyme. With a perfusion rate of 1-10 $\mu$l/min the, concentration of glucose in the tissue may be diluted by a factor of 3-40 by means of a device as described by the invention, which is an optimum glucose concentration for measurement purposes and will help avoid unduly rapid consumption of the glucose-decomposing enzymes and depletion of oxygen at the electrode. In addition, the perfusion fluid could be enriched by oxygen. If electroactive measuring equipment is used, the physical separation between the analyzing unit and the patient's body has the advantage that no catalytic products can be released in the body.

If patients have to monitor regularly certain medical parameters of importance to them, such as blood sugar, they will prefer it to the painful and laborious conventional processes and devices, e.g, the pricking of finger tips in order to gain blood, if they are given a box similar to a pen or handle, to which the subcutaneous needle/catheter may be attached, and in which are contained the unit for feeding and draining a perfusion fluid, the analyzer connected thereto and the evaluation unit, a display unit being connected to the evaluation unit for presentation of the measured parameters. In this instance drug delivery, for example the amount of insulin required, may be determined and administered by the patient himself.

In a further, more convenient variant of the invention, the device additionally contains a drug delivery unit where the subcutaneous needle/catheter already present in used for injecting the drug. In this manner an insulin-dependent patient will be able to determine the glucose value and administer the appropriate dose of the drug with only one insertion of the subcutaneous needle as described by the invention.

In a particularly simple device according to the invention, the plunger pump for the perfusion fluid, the drug feeder pump and, if applicable, the pump for the calibrating fluid, are operated by hand via a lever system.

If the pen-type device is to be carried in the pocket of a jacket or a handbag, a tightly fitting sleeve or cap may be slipped over the needle, or, if the needle is removed, over the mounting stud of the needle, which will keep the needle sterile, prevent evaporation of the perfusion fluid and enable the unused perfusion fluid to return into the analyzing unit upon actuation of the perfusion pump. The perfusion fluid, which in its unused state does not contain any, or only a minute amount of the substances to be analyzed, may thus be used for wetting the measuring capillary of the analyzing unit in order to prevent any damage of the sensors and measuring electrodes due to desiccation. Besides, special agents could be added to the perfusion fluid to obtain even better protection of the analyzing unit. Such additives would include substances which further improve the content of immobilized enzyme if immobilized glucose oxidase or some other enzyme is used. The perfusion fluid can also be used for zero point calibration prior to the next measurement of the patient's values.

No matter whether the pen-type device is configured as a measuring device, for example a "glucose pen", or as a combined measuring/therapy device, for example a "glucose/insulin pen", or as an implantable or portable device, miniaturization of the individual components will be enhanced if the valves required for assigning the individual feeding and draining tubes to the individual reservoirs are combined into a multiway valve, whose valve body contains all feeding and draining tubes and whose movable part has channels or grooves for proper connection of these tubes, individual positions of the movable part being adjusted by means of a setting disk, or automatically via signals of the evaluation unit received at a drive unit. The use of a multiway valve will not only permit all necessary connections of tubes and reservoirs that are described in great detail in the description of the drawings, but will also enable many or all of the necessary switching processes for the individual pumps to be performed via the movable part of the multiway valve.

Among the most important positions of the multiway valve are:

(1) a measuring position, in which the exchange channel of the device is connected to the feeding/draining unit for the perfusion fluid, and in which this unit is connected to the analyzing unit and, if required, the feeding tube for the drug is connected to the drug supply;

(2) a calibrating position (slope), in which the calibrating solution is fed into the analyzing unit;

(3) a calibrating position (zero point calibration), in which new perfusion fluid may be delivered to the analyzing unit;

(4) a position for entering air in order to separate the perfusion fluid from the calibrating solution;

(5) a position in which air bubbles may be entered into the perfusion path in order to divide the perfusion fluid into timed portions;

(6) a position in which the calibrating solution may be entered into the drug feeding tube in order to keep it open even if no drug is administered for some time, or if the calibrating solution contains a substance that is not compatible with the drug.

In order to improve the intake of air entered in operating positions 4 or 5, an additional collecting vessel could be provided in the device. For example, the widening chamber behind the advancing plunger of the drug delivery pump could be used.

An enhanced variant of the invention may envisage that a negative pressure sensor be provided in the drainage tube, or in the tube leading towards the collecting vessel, or in the collecting vessel for the perfusion fluid itself. In case of an obstruction of the perfusion path, the pressure and suction pumps for the perfusion fluid may be switched off or reversed via the negative pressure sensor. The negative pressure sensor is of advantage mainly because of the marked negative pressure prevailing in the collecting vessel during the measuring process, which would cause an excessive amount of air to be taken in after switchover to air intake, thus wasting space in the collecting vessel. This could be counteracted by a short reverse run of the plunger pump before the multiway valve is switched over.

In a preferred variant of the invention, the analyzing unit for measuring the parame of interest to be analyzed and the marker variables is configured as a replaceable unit during whose removal the tubes connected to the analyzing unit may be closed by means of a shutting mechanism, which will help maintain the pressure built up in the tubes, a further advantage being that all containers and reservoirs as well as all feeder and drainage tubes are configured as a dispensable unit located on a common supporting element, such that a flexible connection is automatically established between the drive units for the pumps and the multiway valve when the common supporting element is inserted into the device. In this way all containers and reservoirs may quickly be replaced by a new set.

Finally, another variant of the invention provides that a metering switch be added for regulating the dosage of the drug, which in its first position ensures that the preparation is metered automatically and continuously as calculated by the evaluation unit, while a dose of the drug that is predetermined by the user is administered in the second position. In this way the user has the possibility to administer to himself a large dose of the drug that is effective for several hours. The microprocessor of the evaluation unit could be utilized by the patient to find the suitable size of this does.

Following is a more detailed description of the invention as illustrated by the accompanying drawings.

BRIEF DESCRIPTION OF THE DRAWING

FIG. 1 presents a device as described by the invention,

FIG. 2 is a section in the area of the subcutaneous needle or the subcutaneous catheter, along line II—II in FIG. 1, FIGS. 3–6 show variants of the invention, the sections corresponding to the section in FIG. 2, FIGS. 7a–7f present longitudinal sections and cross-sections of further variants of the subcutaneous needle/catheter, FIG. 7g gives a detail from FIG. 7, FIGS. 8–11 present variants of a pumping device according to FIG. 1, FIG. 12 given another variant according to FIG. 1, FIGS. 13a–13d show valve positions of a multiway valve according to FIG. 12, FIG. 14 gives a detail from FIG. 12, FIG. 15 gives a detail of an implantable device, FIG. 16 shows a variant according to FIGS. 1 and 12, configured as a "glucose pen", FIGS. 17-19 show variants according to FIGS. 1 and 12, configured as "glucose/insulin pens", FIG. 20 presents a calibrating device for the variants of FIGS. 16-19, FIGS. 21, 22 give measurement curves obtained by experiments.

DETAILED DESCRIPTION OF THE PREFERRED EMBODIMENTS

Figure 4:
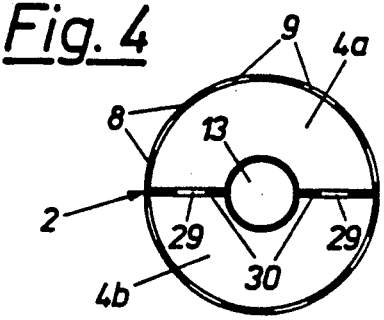

A schematical view of a device for determining the parameters of interest in the tissue of living organisms is presented in FIG. 1. The part 1 to be inserted into the tissue is configured as a subcutaneous needle or subcutaneous catheter 2.

The subcutaneous needle 2 contains an exchange channel 4, which is in direct contact with the surrounding tissue through openings 9, and which communicates with the feeding/draining unit 5 for the perfusion fluid via a feeder tube 3.

After being at least partially equilibrated with the tissue, the perfusion fluid passes through an opening 6 near the tip 1' of the subcutaneous needle 2 into a drainage tube 7 leading into an analyzing unit 10. Ridges 8 between the openings 9 keep the tissue from entering the preformed channel 4.

The analyzing unit 10 may be configured as a two-channel analyzer, for instance for glucose as the parameter of interest and D.C./A.C. conductivity as a marker variable, the computer of the attached evaluation unit 11 utilizing the calculated concentration of tissue glucose to control an insulin pump or other drug delivery pump 12 such that standard blood glucose levels are obtained. The insulin is delivered through a feeding tube 13 to the tip 1' of the needle or catheter, from where it is released into the tissue via one or more drug release openings 14. For the sake of simplicity a joint pumping device may be used, e.g. a roller pump, peristaltic pump, pressure vessel, etc., performing the functions of the pressure pump 15, the suction pump 16 for the perfusion fluid and the drug delivery pump 12. For the perfusion fluid a reservoir 17 and a collecting vessel 18 are provided in the feeding/draining unit, while the drug feeder unit 62 contains a drug reservoir 19. The computer of the evaluation unit 11 may also be used for controlling the optimum working rate of the pressure pump 15 and the suction pump 16 for the perfusion fluid, based on the concentration of the marker substance. Optimum geometrical configuration might permit the perfusion fluid to be delivered through all lines with the use of the suction pump 16 only, whereas delivery by means of the pressure pump 15 only seems to be more of a problem, as an excessive amount of fluid would be pushed into the tissue through the openings 9 in the instance of excess pressure. The composition of the perfusion fluid may be optimized so as to improve the exchange of agents through the openings 9; for instance, a hyper-osmotic or hyper-oncotic fluid may be used, or anti-coagulant agents, such as heparin, or a tissue plasminogene activator may be added. Experiments have shown that simple solutions such as low-ion water or a 5% mannitol solution with heparin as an additive are best. By means of a calibrating unit 20, which is connected to the drainage tube 7 by the connecting tube 22, a calibrating solution from a container 21 may be delivered to the sensors of the analyzing unit 10 with the use of a pump 23, permitting re-calibration of the sensors before each measurement.

In the instance of stable sensors or measuring electrodes the tube 22, the container 21 with the calibrating solution and the pump 23 could be omitted, or the sensors and measuring electrodes of the analyzing unit 10 could be checked outside of the device, especially if the analyzing unit is easy to replace.

The pump 23 for the calibrating solution, the pressure pump 15 for the perfusion fluid, the suction pump 16 for the perfusion fluid to be recovered, and the pump 12 for drug delivery may have the same design essentially, as similar pumping rates in the range of microliters per minute are needed for all pumps. The connecting tube 22 could open into the tube 7' on the other side of the analyzer 10 between the analyzer and the collecting vessel 18 for the perfusion fluid, in which case the direction of perfusion in the analyzer 10 would be reversed. In order to prevent the perfusion fluid from mixing with the calibrating solution, the drainage tube 7 and the connecting tube 22, or rather, the analyzing unit 10 and the collecting vessel should be separated by one or several valves 24, 25, 25a, or rather, by a multiway valve. For this purpose valves could be used which are controlled exclusively by the pressure ratios in the tubes 7, 7' and 22, such that the drainage tube 7 would be closed in case of a pressure rise in the tube 22, permitting the calibrating solution to reach the analyzing unit 10 while prohibiting any mixing with the perfusion fluid in tube 7. In the instance of perfusion of the analyzing unit 10 with perfusion fluid from tube 7, the valves 24, 25 would be switched such that no calibrating solution can reach the analyzing unit 10 from the tube 22. Instead of the pressure-controlled valves, which are pressed into their seats by the fluid stream inside the tubes, other kinds of valves could be used, for example magnetic valves squeezing shut or opening the tubes 22, 7, 7' from outside, for which tubes soft, compressible materials would be suited; in this instance the corresponding valve could be opened or shut by the signal of the computer in the evaluation unit 11, in accordance with the pumping device switched on. No matter whether a multiway valve or valves 24, 25, 25a are employed for this purpose: energy should be used only for switching the valves; once the multiway valve or the valves are switched, no energy need be applied.

In tubes 7, 7' or in the collecting vessel 18 a negative pressure sensor 18' should be located which would indicate any blockage of the perfusion system and could be used to clean the blocked passage by reversal of the fluid stream in the perfusion system.

The entire system of reservoirs, comprising containers 17, 18, 22, and, possibly, 19, as well as 43, if a separate collecting vessel is provided for the calibrating solution, should be configured in such a way as to permit simultaneous replacement of the complete system as a set together with tubes 3, 7, 7', 13 and 22. This would ensure easy handling by the patient and eliminate the danger of confusing individual containers or tubes. In order to make sure that the subcutaneous needle/catheter 2 will remain in the body even when the complete system of containers and tubes is replaced, a joint plug-in connection 26 is provided for tubes 3, 7 and 13, where the replaced system may be connected to the subcutaneous needle or catheter 2. A suitable geometrical configuration of the plug-in connection will prevent confusion of the individual tubes on part of the patient.

The joint plug-in connection 26 could be secured by a threaded fitting, for example a union nut. If an artificial pancreas is to be produced, the analyzing unit 10 may carry a glucose electrode combined with an ion-selective electrode or a conductivity meter. In this way one and the same electronics and, possibly, the same electrodes may be used for both measurements.

The analyzing unit 10 could also be used for conventional chemical methods, in particular, if the required reaction mixture is added to the perfusate before analysis, and if a photometer is employed instead of electrodes, especially in dry chemical measurement processes.

Although the drug for treating a disorder found in the organism could be added to the perfusion fluid in the reservoir 17, it is more economical from the point of view of drug consumption to use a special reservoir 19 and the additional drug feeding tube 13 for this purpose. Besides, the distance between the openings 9 and the drug release opening 14 in the subcutaneous needle 2 should be chosen so as to minimize drug losses via the drained perfusion fluid. In order to prevent the drug introduced into the device from draining through the drainage tube 7, the feeder tube 3, or rather, the exchange channel 4 and the drainage tube 7 at the tip 1' of the catheter or needle 2 have a blind end.

In order to prevent the intake of air through the drainage tube 7 at the site of the puncture in the instance of too large a negative pressure, it is recommended that the direction of perfusion be from the surface of the body towards its depth, as is shown in FIG. 1. Any intake of air through the tube 7 would be detected by the conductivity meter or ionic sensor in the analyzing unit 10, which could not only signal alarm but could also initiate the necessary steps, such as reduction of the perfusion rate, reversion of the direction of pumping, etc. A sealing collar 2' around the subcutaneous needle 2 could provide further protection against the intake of air through the skin puncture. For disturbance-free recovery of perfusion fluid the pressure pump 15 and the suction pump 16 should be designed so as to enable similar or identical quantities of perfusion fluid to be pumped into the body and withdrawn again per unit of time, which is best achieved by combining pumps 15 and 16 into an integrated unit.

FIG. 2 shows an example of a subcutaneous needle/catheter 2 based on a section in FIG. 1. The drainage tube from the preformed channel 4 is marked 7, the opening into the drainage tube 7 is marked 6. For maximum extension of the exchange surface interacting with the surrounding tissue the channel 4 may be configured as an annular passage surrounding the drainage tube 7 and the drug feeding tube 13. The ridges 8 separate numerous openings 9 of the channel 4, which represent the equilibration surface towards the tissue.

FIG. 3 shows a cross-section of a further variant of a catheter, the exchange channel 4 being segmented by numerous septa 27 along the length of the catheter. Dividing the channel 4 into capillary sectors by a number of septa 27 has the advantage that a maximum exchange surface is obtained in the areas 9' between the septa 27, while ensuring that the tissue is supported by these septa and thus prevented from entering the path of perfusion. The septa 27 could also be helical in shape in order to extend the equilibration path even further. The catheter 2 — in particular if parts or all of it are made of a flexible material — is inserted into the tissue by means of a hollow needle 28, which latter is removed from the tissue after puncturing while the catheter will remain. One or more openings 6 are provided at one end of the needle/catheter 2 preferably, where the septa may be omitted from the surface of tubes 7 and 13, such that the perfusion fluid may enter the drainage tube 7 from all capillary sectors through at least one opening 6.

FIG. 4 shows another possible variant in which the subcutaneous needle/catheter 2 contains the drug feeding tube 13 and the preformed channel 4 is divided into two parts by a partition wall 30. The part of the preformed channel 4 marked 4a is connected with the feeder tube 3 not shown here. At the level of section II—II in FIG. 1 channel 4a connects to its second part 4b by means of the openings 29, which part 4b is connected to the drainage tube. Due to this configuration both parts may be utilized for equilibration; care should be taken, however, to prevent a shunt of the perfusion fluid outside the needle, since such a shunt would not allow use of the entire length of the needle for equilibration purposes. This variant could also be configured with a through-going partition wall 30 without a drug feeding tube 13.

Figure 5:
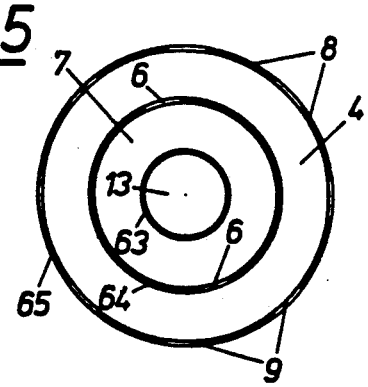

FIG. 5 presents a variant of the subcutaneous needle/catheter 2 in which three cylindrical cannulas 63, 64, 65 are arranged concentrically one within the other. The innermost cannula 63 acts as the feeding tube 13 for the drug entering the body from the open end of this cannula. The cannula in the middle 64 is used for delivering the perfusion fluid, the outer cannula 65 serving as a preformed channel 4. The opening 6 between the channel 4 and the tube 7 preferably is located near the tip of the needle, i.e. at the distal end of the needle, such that the entire length of the subcutaneous needle may be utilized as a perfusion path. The middle and outer cannulas are closed off at the end of the needle. The arrangement shown here can be fabricated easily, permitting very thin walls with only capillary gaps between the concentric cannulas 63, 64, 65.

Figure 6:
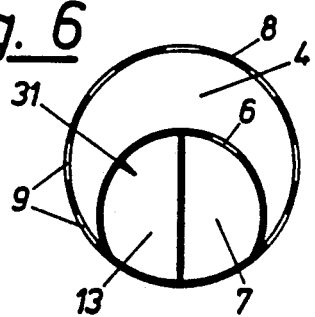

FIG. 6 shows a variant of the subcutaneous catheter or needle 2 in which the inside is divided into three compartments by means of a branched septum 31 or two septa, one compartment being configured as a preformed channel 4 connected to the feeder tube 3. The septum 31 should be configured such that as large a part of the circumference of the needle as possible can be used as a perfusion path. Although part of the needle surface cannot be utilized for equilibration in this instance, the smaller amount of material required, and thus a thinner needle or cannula causing less discomfort upon puncturing, will make up for this.

Figure 7A:
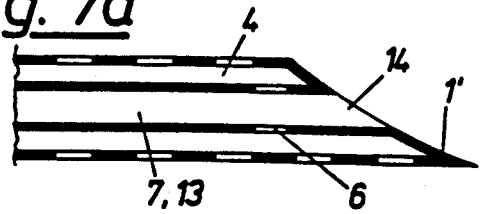
Figure 7F:
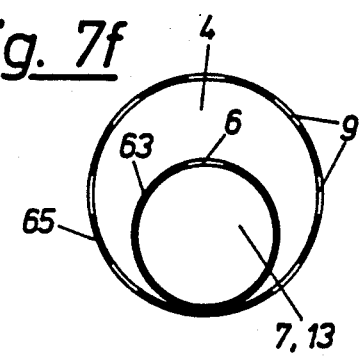
Figure 7B:
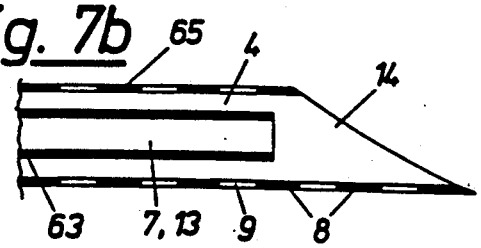
Figure 7C:
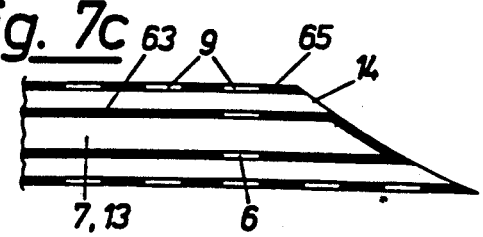
Figure 7E:
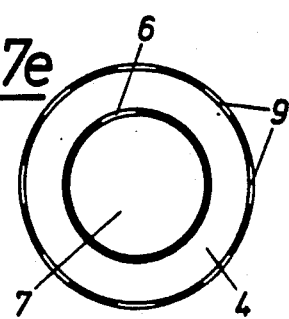
Figure 7D:
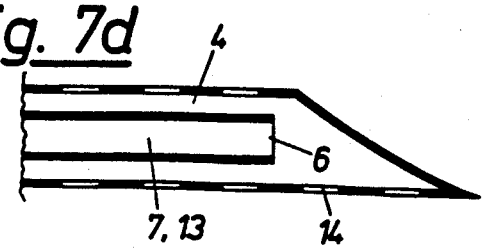

FIGS. 7a to 7f present further possible variants of subcutaneous needles 2, FIGS. 7a–7d showing longitudinal sections corresponding to the part 1 in FIG. 1, and FIGS. 7e–7f cross-sections corresponding to FIG. 2.

If the needle is to be inserted into the body repeatedly, the diameter of the needle or catheter should be as small as possible. In some instances it will suffice for obtaining a perfusion path and a feed passage for application of the drug to use a two-channel subcutaneous needle/catheter as presented in FIGS. 7a–7f, with a drug release opening 14 being possibly provided near the tip 1' of the needle. During perfusion of the needle or catheter the perfusion fluid is passed through the preformed channel 4 in a conventional manner, entering the drainage tube 7 through one or more openings 6 due to the suction effect at the end of the perfusion path. The drainage tube 7 may also serve as a drug feeding tube 13 if it is used intermittently in order to force the drug through the tube 7 to the opening 14 by means of higher pressure. After application of the drug the perfusion fluid may be used to flush any residues of the drug out of the needle, ensuring that the patient is given the entire dose calculated for him. During the perfusion process the drug release opening 14 would be no impediment, as it would be closed by the tissue surrounding it due to the negative pressure in tube 7.

A simple model of a two-channel subcutaneous needle/catheter, which is particularly easy to produce, is shown in FIG. 7b. In this variant a smaller cannula 63 is inserted into a larger cannula 65 with lateral openings 9. Before the smaller cannula 63 forming the drainage passage 7 is inserted, the necessary openings 9 may easily be made in the larger cannula 65, for instance with the use of a high energy beam, such as a laser beam. It is recommended that several rows of openings be made, with mirror-symmetrical openings 9 on the opposite side of the cannula. The inner cannula 63 should not be allowed to touch the tip 1' of the outer cannula 65 in order to prevent the latter from being blocked by the surrounding body tissue.

Variants are possible of course in which the innner cannula 63 is closed (cf. FIG. 7c) and the drug enters the tissue through the opening 6 and the annular opening 14 of the outer cannula 65 near the tip 1' of the needle.

Finally, a variant 7d similar to that in FIG. 7b is conceivable in which the outer cannula 65 is provided with a cover forming the tip 1', and the drug is discharged through openings 9 near the tip 1'.

As is shown in FIG. 7e, the drainage passage 7 may be arranged in the center of the subcutaneous needle, in which instance the entire circumference of the needle may be utilized as an equilibration path, or — as shown in FIG. 7f — the needle may be subdivided into a preformed channel 4 and a drainage passage 7, the inner cannula 63 touching the outer 65. In this instance the openings 9 may be distributed along most of the circumference of the subcutaneous needle, except where the drainage passage 7 is in contact with the outer cannula 65.

Figure 7G:
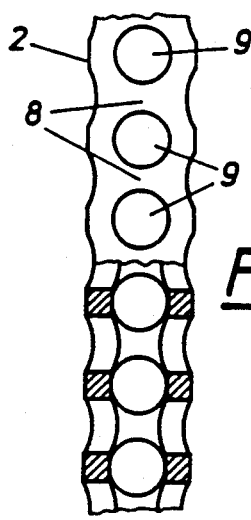

FIG. 7g shows the arrangement of the openings 9 of a subcutaneous needle 2 in detail. Suitable dimensions of such a needle would be a minimum outer diameter of 0.5 mm and a length of 20–30 mm for example. This needle may be provided with openings 9 over a length of 18 mm, for instance in four rows of holes of 0.12 mm diameter distributed over the circumference, which — if placed along the length of the needle, each at a distance of 0.6 mm from the next (distance between centers of bores) — would give about 30 bores in a row, and thus a total of approx. 120 bores, with an exchange area of at least $0.0113 \times 120 = 1.36$ squ.mm. Inside the subcutaneous needle, which could have an inner diameter of 0.3 mm, another hollow cannula with an outer diameter of 0.2 mm and an inner diameter of 0.1 mm may be placed. The volume contained by the needle/cannula in the perfusion path is less than 1 $\mu$l in this case. As regards the process of manufacturing, the two bores opposite each other could be made in one step, and the bores at a 90 degree angle with the first pair could be made in a second step. In order to leave enough material at the wall of the needle and to ensure the necessary rigidity and resistance to breaking, the openings rotated through an angle of 90° along the circumference should be shifted along the longitudinal axis as is shown in the illustration. It would also be possible of course, to use a helcial arrangement of openings 9 in one or more rows.

In a further variant the exchange surface may have openings with diameters of only 80 $\mu$m, i.e. significantly smaller than the inner diameter of the drainage passage. The advantage of this is that any tissue particles which may enter the needle through the openings, cannot block the drainage passage. Besides, the drainage tube 7 could be provided with several openings at its end as an even better safeguard against obstruction.

As is seen in FIG. 1, the device comprises a number of containers for the perfusion fluid, the calibrating solution, the drug, and for collecting the fluids used, as well as several pressure and suction pumps. In order to permit a small, portable model and to simplify the design of the pumps, a design is presented in FIG. 8 in which the pump may simultaneously act as a pressure pump 15 and a suction pump 16. In this illustration 32 refers to a plunger pump whose plunger 33 reduces the volume 36 in front of the plunger upon a forward movement of the driving rod 34, effected e.g. by means of a friction wheel 35, while creating a vacuum in the plunger chamber 37, since the bottom of the plunger pump 32 is provided with a cover 38 enabling the chamber 37 to be used as a collecting vessel 18 at the same time. For this purpose the cover 38 must be sealed against the driving rod 34, for example by means of an O-ring 39. By using the space 37 vacated by the plunger as a collecting vessel the set-up will require less space, and only one pump will be necessary for performing both pumping and suction functions. The different pumping and suction volumes of this pump which arise from the fact that the driving rod 34 is only contained in chamber 37, need not necessarily be a disadvantage if different volumes are required for reservoirs and collecting vessels.

Figure 8:
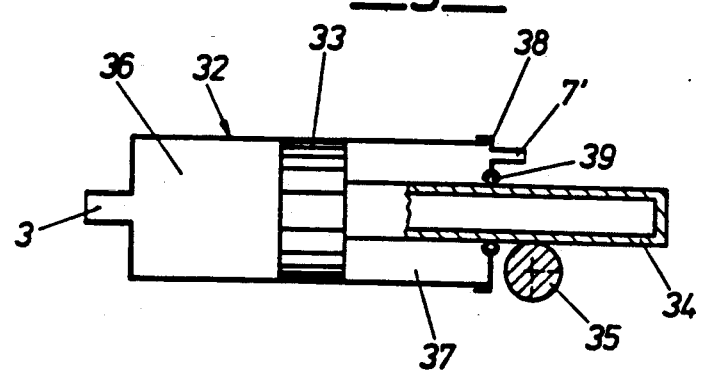
Figure 9:
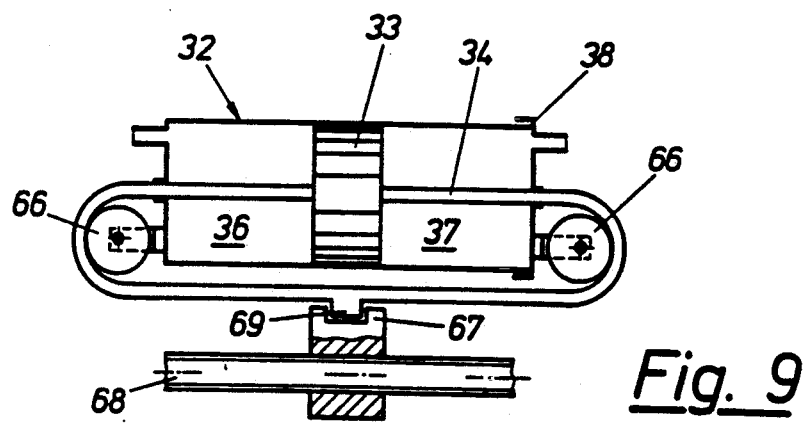

Further reduction of the outer dimensions of the pumping/suction device is achieved by configuring the driving rod 34 as a flexible element (cf. FIG. 9), and by folding it back along the length of the plunger pump 32 by means of deflecting elements or rollers 66, sealing it by a further O-ring and taking it back to the plunger 33 through the chamber 36. In this way a most compact pressure and suction device may be obtained, using a single drive, for instance a friction wheel 35, as shown in FIG. 8. The variant with the driving element 34 on both sides of the plunger 33 has the advantage of identical pumping and suction volumes. The flexible driving element 34 als may be configured as a string or as a plastic element made integral with the plunger 33. The driving element 34 may be driven via a nut 67 moved by a spindle or screw 68. When the pressure/suction device is replaced the driving element 34 may lock with the nut 67 via a projection 69, which will permit the entire driving gear comprising the nut 67 and the screw or spindle 68 to remain in the device. If the driving element 34 is devised as an element that is both flexible and compressible, the O-rings required for sealing the driving element 34 against the cover 38 of the housing may be omitted. Thus the driving element 34 might be made of two materials, for example teflon for a flexible core of high tensile strength and a compressible material such as silicone.

Figure 10:
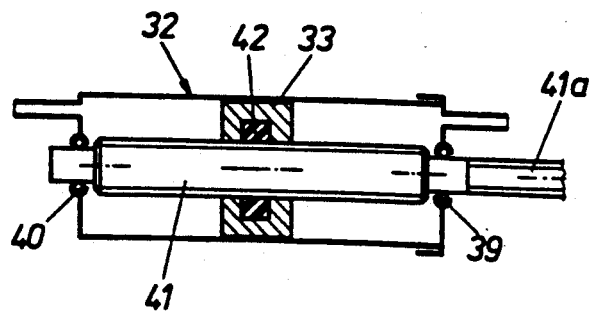

FIG. 10 shows yet another variant of a plunger pump, in which the driving element 34 is configured as a threaded part 41 and is turned on its outer free end 41a, for example by a friction wheel. The plunger 33 is kept from rotating together with the driving element 34 by a particular shape (e.g. tetragonal or polygonal or oval instead of circular) or by the frictional forces prevailing at the wall of the plunger pump 32, such that the rotatory motion of the element 34 is transformed into a longitudinal motion of the plunger 33. This device, which uses up a minimum of space, is easy to make if the thread has smooth parts on both ends, as shown in FIG. 10, i.e. where the driving element 34 leaves the plunger pump 32, such that it may be sealed against the wall of the pump 32 in these parts, for example by O-rings 39 and 40. It may be necessary to provide a further sealing 42 between the plunger 33 and the driving element 34. If the plunger 33 is made of suitably flexible material, however, the additional sealing may usually be omitted.

Figure 11:
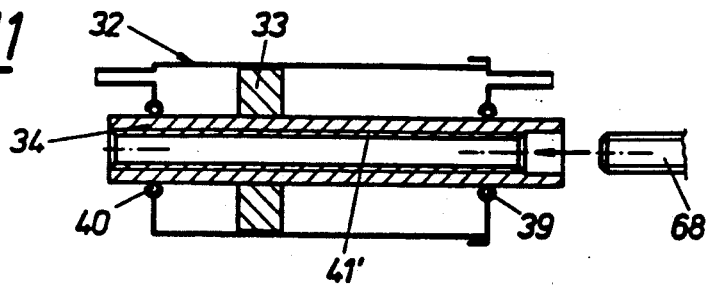

FIG. 11 shows a further variant as a modification of FIG. 10. In this variant the driving element 34 is hollow, with a thread 41' on its inside, to which is imparted either a forward or a backward motion by a screw 68, depending on the sense of rotation, thus moving the plunger 33 either forwards or backwards. A suitable shape of the plunger 33 in the housing again will prevent the driving element 34 and plunger 33 from rotating. In this variant the pumping and suction volumes again are identical.

Figure 12:
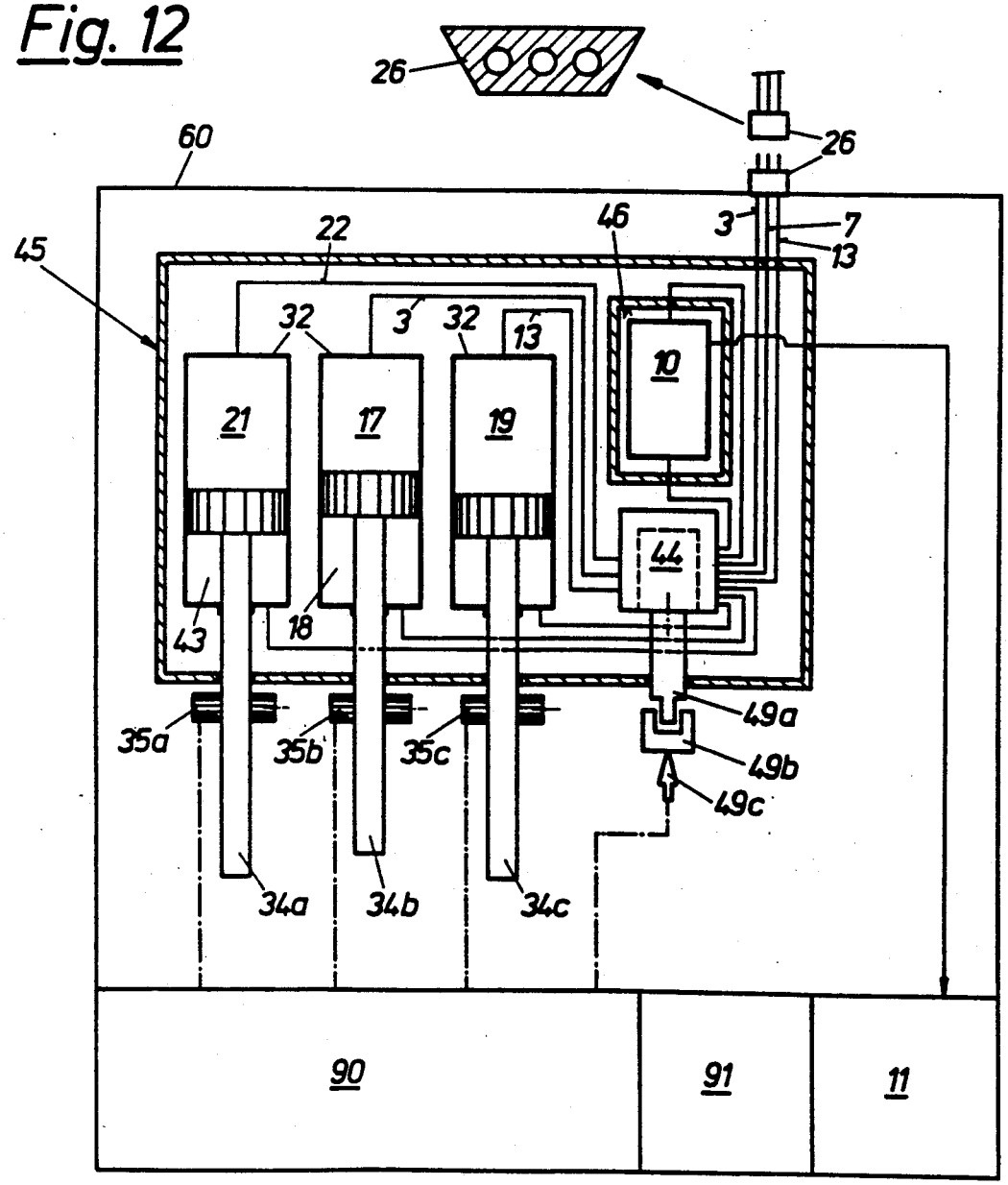

In order to simplify handling of the device by the patient, it is possible to combine all replaceable parts in a complete one-time set which may be replaced. FIG. 12 shows such a replaceable unit. The reservoir 19 for the drug, the reservoir 17 for the perfusion fluid, the collecting vessel 18 for the used perfusion fluid, the container 21 for the calibrating solution, the collecting vessel 43 for the calibrating solution, as well as a multiway valve 44 to be described in more detail below, all are located on a joint supporting element or in a joint housing 45, which will not only seal all solutions and fluids in the system against the electronics in the device, but will also permit easy handling by the patient. All the patient needs to do is exchange the whole supporting element 45 for a new one and insert it into the housing 60. Via the joint plug-in connection 26 the lines 3, 7, 13 are connected to the subcutaneous needle not shown here. The three driving elements 34a-34c of the plunger pumps 32 are automatically put into contact with the drive, i.e. in this case with the friction wheels 35a-35c, when the supporting element 45 is inserted into the housing 60. The analyzing unit 10 may also be mounted on the supporting element 45 and be replaced together with it, or it may be placed in a recess 46 of the supporting element 45, where it can be replaced separately. The driving unit 90 (only shown schematically in this drawing) has a power supply 91 and is used for actuating the friction wheels 35a-35c in the manner indicated by the dash-dotted line. It will also be possible of course, to have separate motors for driving the individual pumps or friction wheels 35a-35c. The drive of the multiway valve has the reference number 49a-c.

FIG. 13 gives a section of a detail of a multiway valve 44, which will establish the following connections by way of several independent channels 61 located in the moveable part 49 configured as a rotating body. The reference numbers enclosed by circles indicate the vessels and components which may be assigned to the system via the multiway valve.

Figure 13A:
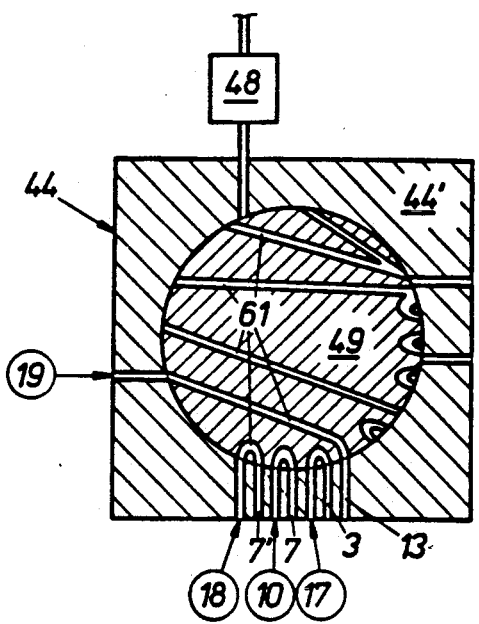

In the position shown in FIG. 13a connections are established simultaneously between the reservoir 17 for the perfusion fluid and the feeder tube 3, between the drainage tube 7 and the analyzing unit 10, between the tube 7' departing from the analyzing unit 10 and the collecting vessel 18, and between the drug reservoir 19 and the drug feeding tube 13.

Figure 13B:
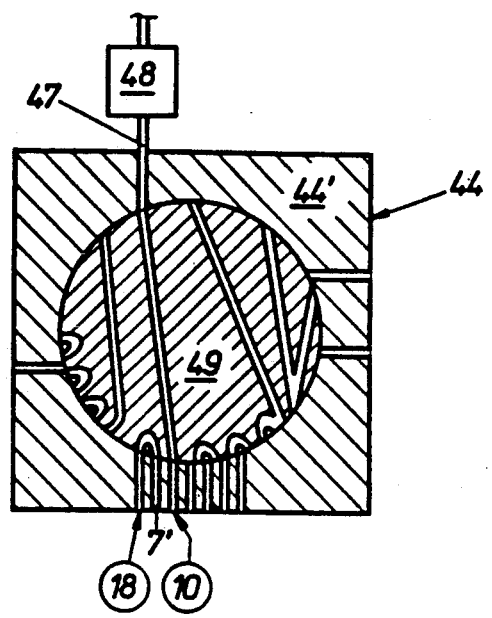

In FIG. 13b connections are established between an opening 47 located in the valve body 44' and are open to the ambient air, and the analyzing unit 10, as well as between the tube 7' and the collecting vessel 18.

Figure 13C:
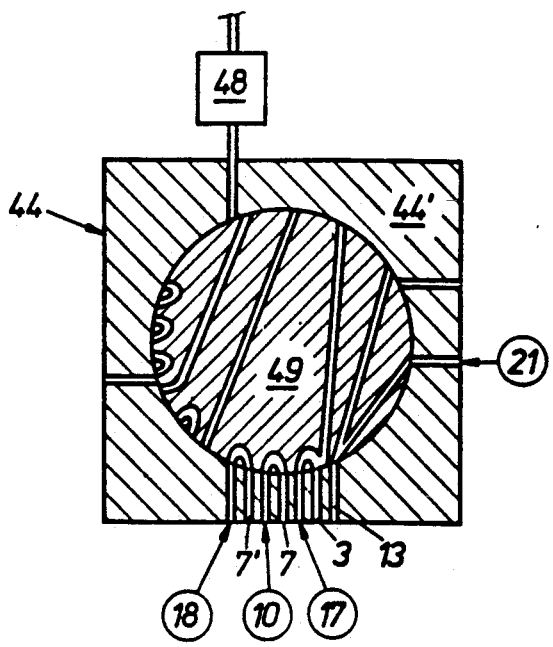

In the position shown in FIG. 13c connections are established simultaneously between the perfusate reservoir 17 and the feeder tube 3, between the drainage tube 7 and the analyzing unit 10, between the tube 7' and the collecting vessel 18, and between the container 21 for the calibrating solution and the drug feeding tube 13.

Figure 13D:
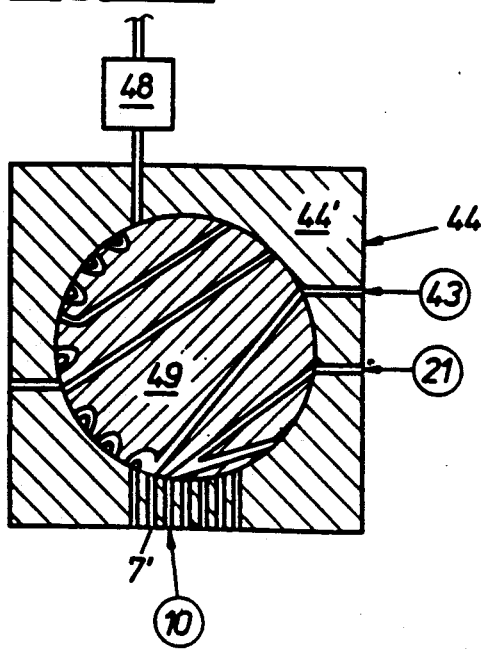

In the position shown in FIG. 13d connections are established simultaneously between the container 21 for the calibrating solution and the analyzing unit 10, between the tube 7' and the collecting vessel 43 for the calibrating solution.

The design described above, or a similar one, has the advantage that the use of a single multiway valve, and thus a single rotation will permit analysis of the perfusion fluid by means of the analyzer 10, or re-calibration of the sensors of the analyzer 10 by means of the calibrating solution.

The position shown in FIG. 13a serves for perfusion of the subcutaneous needle, the perfusion fluid recovered being continually tested by the analyzing unit 10, and the computer of the evaluation unit 11 continually applying the required dose of the drug via the connection established between the drug reservoir 19 and the needle.

In the position shown in FIG. 13b an air bubble is taken in through the opening 47 between the calibrating process and the analyzing process, in order to prevent the perfusion fluid to be analyzed from mixing with the calibrating solution. At the same time the multiway valve may replace a valve 25a (FIG. 1) closing or opening the analyzing unit 10 relative to the collecting vessel 18 or 43.

In the valve position shown in FIG. 13c the exchange channel is supplied with perfusion fluid from the reservoir 17 via the feeder tube 3, which fluid is then equilibrated and conveyed to the analyzing unit 10 through the drainage tube 7; instead of the drug from the reservoir 19, the container 21 with the calibrating solution is connected to the drug feeding tube 13. If the device is used as an artifical pancreas for instance, the supply of insulin through the tube 13 might have to be interrupted for a certain period of time in case of an excessive drop of the blood sugar level, which might block the drug release opening in the needle. This could be prevented by keeping the passage 13 open with the use of some other fluid, as is shown in FIG. 13c. In case of an unduly low level of blood sugar it might be adviseable to feed a substance increasing the blood sugar content, e.g. glucagon, which could be added to the fluid keeping open the passage 13 and the drug release opening 14. In certain instances the perfusion fluid might be suitable for keeping open the drug feeding tube 13, above all, if the sensors and electrodes of the analyzing unit 10 are sufficiently stable and need not be re-calibrated. In this instance the additional container for the calibrating solution could be omitted.

During the calibration process according to FIG. 13d the calibrating fluid is delivered from the container 21 into the analyzing unit 10, from where it enters the collecting vessel 43 through the tube 7'. Another important valve position, which is not shown here, will establish a connection between the container for the perfusion fluid and the analyzing unit, bypassing the perfusion fluid line, in order to perform a zero-point calibration by means of a low-ion, low-glucose perfusion fluid.

Since the air which is drawn in in the position shown in FIG. 13b for example, will come into contact with the fluids in contact with the living organism, a bacteriological filter 48 may be inserted at the point of air entrance, e.g. in opening 47. The course of the passages 61 in the movable part 49 of the multiway valve 44 is represented only schematically and is only intended to indicate the practicability of such a multiway valve. In practice the passages 61 will be arranged on different planes, thus obtaining a straight course free of intersections. In another variant the passages 61 could be replaced by grooves along the surface of the rotatable part 49 in order to establish the necessary connections.

It should be pointed out here that the multiway valve 44 may fulfill a number of other important functions, such as reversing the direction of flow of the perfusion fluid in the subcutaneous needle, etc.

In any intermediate position of the multiway valve 44 the analyzing unit 10 is separated both from the drainage tube 7, or rather the container 21 holding the calibrating solution, and from the tube 7' leading into the collecting vessels 18 and 43, which will enable the analyzing unit to be replaced without any change of the pressure ratio in the tubes or containers. The advantage of this is that a negative pressure or high pressure will be maintained, once it has been built up for transport of the fluid. If it had to be built up again space would be lost in the individual containers. The positions of the multiway valve 44 presented in FIGS. 13a–13d could also be used for driving a gear system in such a way that each valve position would actuate the pumps corresponding to a particular operational state. In the position shown in FIG. 13a for example, the drive 35b for the perfusate pump and, possible, for the drug delivery pump, would be actuated, in the valve position shown in FIG. 13b the drive 35a for the perfusate pump would be actuated. In the position shown in FIG. 13c the perfusate pump and the pump for the calibrating solution would be actuated. In the valve position shown in FIG. 13d the calibrating pump alone could be actuated. This the device may be operated by means of a single drive unit 90 and its power supply 91 (cf. FIG. 12), which would perform all mechanical functions via toothed racks or a system of levers not shown here in detail. The supporting element 45 comprising all containers, pumps, tubes and the multiway valve may easily be coupled to the drive unit 90, as is shown schematically in FIG. 12, since placing the supporting element in the device will not only provide the friction-wheel drives for the driving elements of the pumps, but also a coupling to the multiway valve 44. The latter may be put into contact with the drive unit 90 via a hub 49a engaging in the drive 49b. In order to ensure proper connection between the drive 49b and the multiway valve 44 regardless of the valve position, the hub 49a and its counterpart, the drive 49b, are designed asymmetrical and are additionally provided with a spring 49c, such that the hub 49a will only engage in the drive 49b if the position of the two parts relative to each other is correct.

FIG. 14 presents the analyzing unit 10 as a block which may be replaced separately in case of a failure. In its inserted state the measuring capillary 50 of the analyzing unit 10 is sealed against tubes 7 and 7' by means of O-rings 51. In order to make sure that the drainage tube 7 and the tube 7' into the collecting vessel are sealed when the analyzing unit 10 is removed, and thus to prevent a pressure loss in the system, a shutting mechanism 52 is provided, which will squeeze shut the tubes 7, 7' via springs 53. When the analyzing unit 10 is inserted into the recess 46 of the supporting element or housing 45, the electrical lines 54 of the individual sensors and measuring electrodes 10' of the analyzing unit 10 are automatically connected to the electrical lines 55 towards the evaluation unit 11 via electrical contacts 56.

The entire device may also be configured as an implantable unit, by providing a preformed channel 4 on the surface of the implanted device and by using large portions of the surface as an equilibration area. In such an implantable device the reservoirs 17 and 19 for the perfusion fluid and the drug could be refilled transcutaneously by means of a needle via a septum 57, as is shown in FIG. 15. By enlarging or reducing the volume of a reservoir when refilling or draining it, for instance reservoir 17, parts of whose walls 58 are flexible, a mechanical element 59, for example stamps which are fastened to the wall of the reservoir, may be actuated, thus keeping the exchange channel 4 on the surface of the device free from ingrowing tissue particles. The skin would have to be punctured only from time to time in order to refill the reservoirs for the perfusion fluid or the drug. In this variant the collecting vessel for the used perfusion fluid could be omitted, as the small fluid quantities may be absorbed by the tissue after the measuring process. It should be noted that the examples given here are only some of the variants possible with this device.

As is known successful efforts have been made to inject drugs in to the body with the use of hand-operated pumps. For example, devices have been built in which an ampoule containing a drug is inserted in a pen-shaped housing and in which the plunger of the ampoule may be pushed forward by the desired distance by means of pressing a lever or turning a wheel, thus injecting a precisely defined amount of the drug into the body.

FIG. 16 gives an example of a "glucose pen" with a pen-shaped housing 70 provided with a subcutaneous needle 2 on one end. Inside the housing there is a plunger pump 32 with a reservoir 17 for the perfusion fluid, from which the perfusion fluid may be pumped into the needle or delivered to the collecting vessel 18 by means of the plunger 33. The plunger may be actuated by hand with the use of a lever 71 and, if necessary, a gear 72 (shown schematically in this illustration), and the perfusion fluid may be delivered in the described manner to the openings 9 of the subcutaneous needle 2 and collected again in vessel 18 through the drainage tube 7 by means of the prevailing suction. As close to the subcutaneous needle as possible the analyzing unit 10 is placed together with the measuring capillary 10' for the substance to be analyzed and for the marker substance or marker variable. In this way a fluid may be pumped through the subcutaneous needle 2 for a short period of time, e.g. 1 minute or less, and collected through the openings 9 after it has been equilibrated. After a short interval the actual concentration of the substance of interest, such as blood sugar, prevailing in the tissue may be indicated by a display unit 73 or an acoustic alarm, after having been calculated by the evaluation unit 11 from the marker variable, e.g. the concentration of the marker substance, and the concentration of the substance of interest. In order to obtain a uniform flow-rate during the time required for perfusion of the tissue several methods could be employed. For example, a uniform flow-rate may be achieved via the lever element 71 whose lever is repeatedly actuated during the perfusion period. The lever could be returned into its initial position by means of a spring 74 (shown schematically) or some other energy-storing element. The perfusion rate during the collecting period could be in the range of 1 to 10 μl/min.

Another possibility, which probably is more attractive, would be to charge an energy-storing element by actuating the lever 71 once or several times, which in turn will uniformly drive the gear 72 during a subsequent time interval, thus effecting fluid transport. The device described here could also be provided with some other source of power, for instance a motor. In order to obtain an immediate measurement result, which would allow early removal of the subcutaneous needle from the tissue, the distance between subcutaneous needle 2 and analyzing unit 10 should be kept as short as possible by placing the measuring capillary 10' very close to the plug-in connection 26 of the subcutaneous needle/catheter 2, as is shown here. The capacity of the measuring capillary 10' should be a few μl or less in order to permit instantaneous analysis. The sensors or the measuring electrode for the marker substance or marker variable could signal adequate filling of the measuring capillary 10' and/or adequate equilibration, for example by optical or acoustic signals, indicating that the pumping process can be terminated.

The complete set comprising the reservoir 17 and the collecting vessel 18 for the perfusion fluid and, possible, the analyzing unit 10, should be configured as a one-time set which may be removed from the "glucose pen" after unscrewing the threaded part 75 of the housing 70, and may be replaced by a new set. After the measuring process the dose of insulin required may be adjusted to the level of blood sugar last determined, and administered with the use of a conventional drug applicator.

A glucose pen could also be mounted piggyback on an insulin pen, as is shown in FIG. 17. In this instance both devices, the glucose pen 76 and the insulin pen 77 are connected to the same subcutaneous needle 2 via the plug-in connection 26, and a multiway valve 44 may be directly connected to the plug-in connection 26 in order to connect the subcutaneous needle 2 alternatingly to the glucose pen 76 and the insulin pen 77. Thus one and the same needle may be used for measuring the disorder in the body and to remedy that disorder by injection of a drug.

FIG. 18 shows a variant in which the glucose pen and the insulin pen are not coupled to each other but are located in a joint housing 70. The one-time set, comprising a drug reservoir 19, a reservoir 17 for the perfusion fluid and, possibly, the analyzing unit 10, again may be replaced as a whole.

Of course a separately replaceable analyzing unit could be provided outside of the housing 70, adjacent to the plug-in connection 26; in this instance the device would basically consist of four easily separable parts arranged one behind the other, depending on their frequency of replacement. The topmost part is formed by the permanent mechanism comprising the combined evaluation/display unit, followed by the containers and pumps combined into a disposable set which — if suitably configured — may form part of the housing, followed by the plug-in analyzing unit, which in turn is followed by the subcutaneous needle, i.e. the most frequently replaced element of the device.

In FIG. 19 presenting a view of the outside of a slightly modified variant of the device, 78 refers to a setting disk, by which the gear 72 may be switched either to the plunger 33 of the reservoir 17 for the perfusion fluid or to the plunger of the drug reservoir 19. At the same time a multiway valve 44 (if present) may be actuated by the disk. By means of the setting disk 78 the gear may be switched from the measurement position (M) to the drug application position (e.g. I for insulin) or to the flushing position (S) for flushing the subcutaneous needle after the drug has been applied, or to the calibrating position (E). If a multiway valve is used it should be designed so as to be replaceable together with the reservoirs and collecting vessels.

Instead of a single lever element 71 two may be used, as is shown in FIG. 17, by which the plungers of the two reservoirs 17 and 19 may be moved separately. Instead of the plunger pumps any other type of pumps may be employed. On the display 73 of the housing 70 the value calculated by the evaluation unit 11 is given. It should be pointed out here that in certain instances the diffusion constants of the marker substance and the substance of interest should enter the calculation and display of the final concentration of the substance of interest, for which purpose a microprocessor in the evaluation unit might be used.

Furthermore it would be possible to mount a multiway valve 44 on the front end of the pen-shaped housing 70 between the subcutaneous needle 2, or rather, the plug-in connection 26 and the housing 70, which will provide a particularly simple facility for switching the fluid path. In the instance of a subcutaneous needle with three channels (cf. FIGS. 2-6), however, the fluid path need not be switched at this point, since the perfusion path and the drug supply are independent of each other.

Since the variant of the device presented in FIGS. 16–19 is in contact with the body for short periods of time only (i.e. via the subcutaneous needle), and is ready for inspection in between, calibration of the analyzing unit may be performed easily. As is shown in FIG. 20, the device presented in FIGS. 16–19 may be introduced into a calibrating vessel 79 which is filled with a calibrating solution and contains the components required for calibration in the desired concentration. The calibrating vessel 79 has an opening 83 whose shape corresponds to that of the plug-in connection 26, such that the connecting stud 84 of the needle on the housing 70 may be sealed tightly to the vessel 79. Via the pumping device of the glucose pen or glucose/insulin pen the calibrating solution is delivered to the analyzing unit 10. The calibrating vessel 79 is divided into compartments 80, 82 by means of a partition wall 81, thus preventing the perfusion fluid leaving the device from mixing with the calibrating solution in the compartment 80. The partition wall 81 could be made of flexible material, thus avoiding any problems due to excess pressures or negative pressures in one of the compartments 80, 82. An asymmetrical opening 83 of the calibrating vessel 79 will prevent faulty connection of the vessel.

Figure 21:
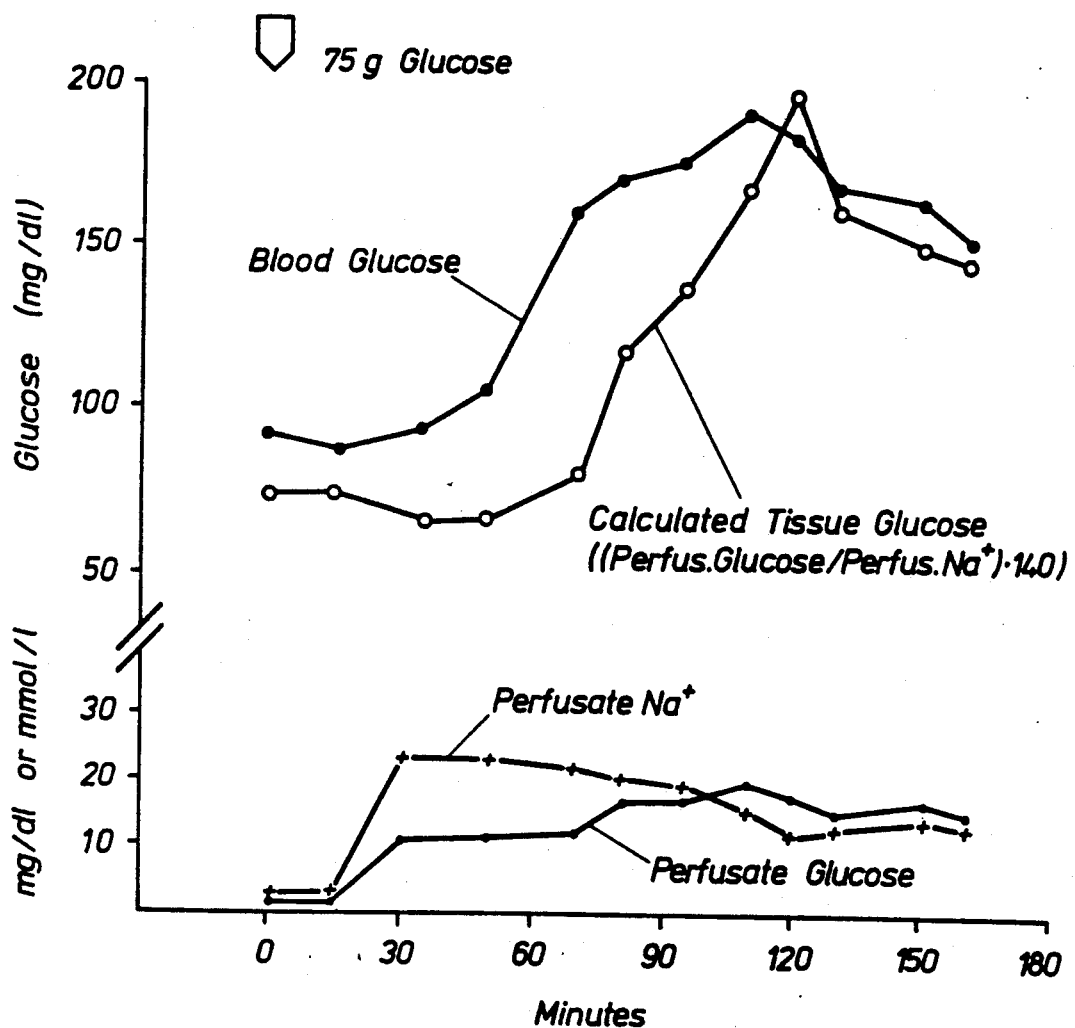
Figure 22:
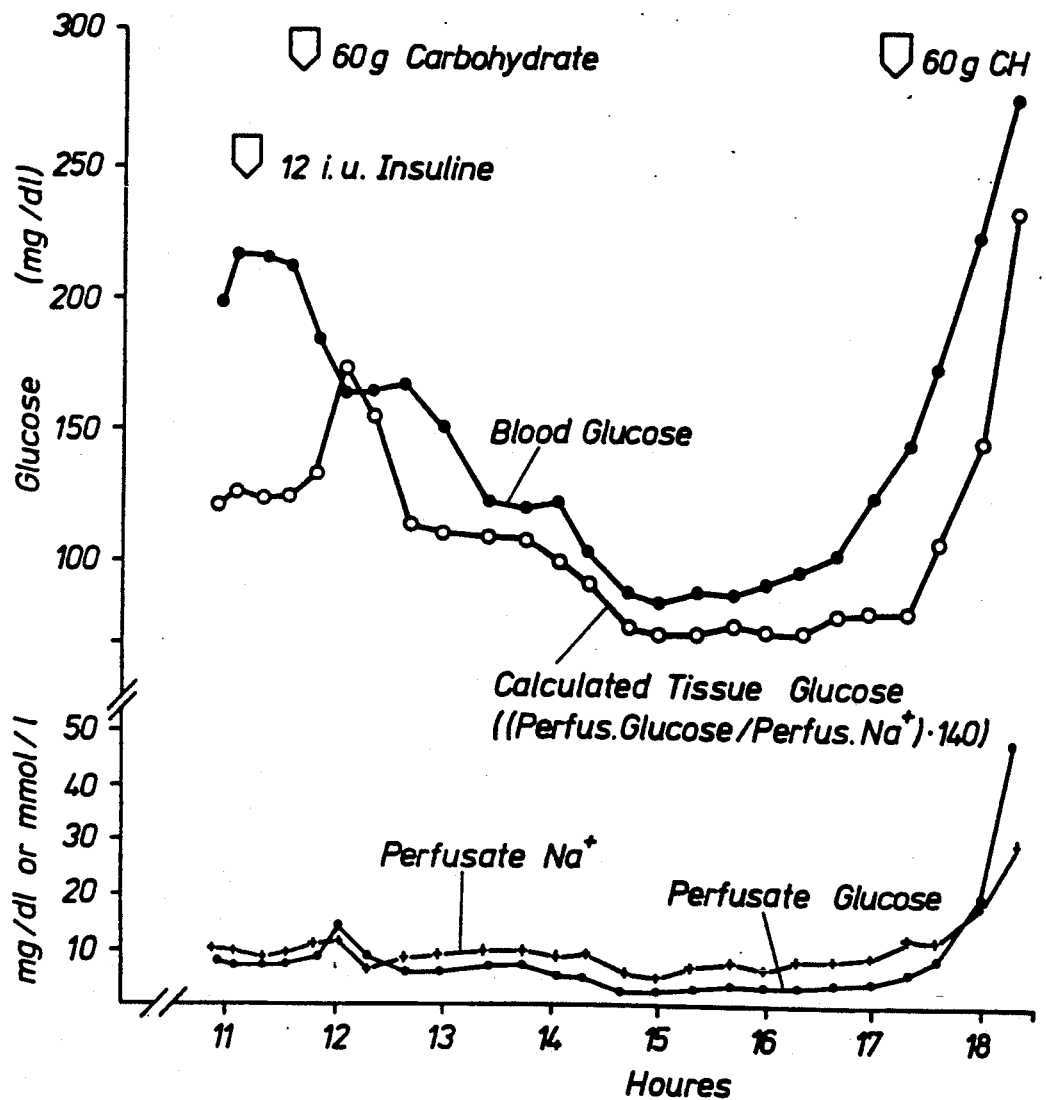

In the diagrams presented in FIGS. 21 and 22 time in hours or minutes is plotted on the abscissa, and the concentration of glucose or Na+ in milligrams per deciliter or mmole per liter is plotted on the ordinate.

FIG. 21 gives a comparison of a curve of tissue glucose calculated by means of the method of the invention and a curve of blood glucose obtained by a conventional method. As can be seen in the lower half of the illustration the concentration of sodium ions in the recovered perfusion fluid is 2-25 mmole/Depending on changing physical factors the concentration of sodium ions will fluctuate considerably, pointing to a non-uniform degree of equilibration. A test taking into account only the glucose concentration in the perfusion fluid is most unsatisfactory for this reason. Only by determining a marker variable — the concentration of sodium ions in this instance — fluctuations in the degree of equilibration may be compensated. As is seen the concentration of glucose in the perfusion fluid is 2-30 mg/dl, i.e. in an optimum range for the enzyme electrode.

As can be seen in the upper half of the illustration the calculated concentration of tissue glucose is in accordance with the measured concentration of blood glucose. The values calculated for tissue glucose are somewhat lower than the values for blood glucose simultaneously obtained. The reasons for this difference are;
(1) glycolysis in the perfusion fluid due to glycolytic enzymes entering the fluid from the tissue;
(2) analysis in this experiment is performed off-line rather than on-line, the perfusion fluid thus accumulating the 15 minutes before being analyzed. This will partly explain the difference between the blood glucose curve and the calculated tissue glucose curve over time. Other experiments have shown that the two curves may match even better by the addition of competitive substrates for ATP. The test curves in FIG. 21 show values of a healthy control subject after oral administration of 75 g glucose.

FIG. 22 shows another set of curves giving a comparison of blood sugar and tissue sugar concentrations in a patient with type 1 diabetes mellitus. As is seen in the lower half of the illustration the concentrations of sodium ions in the perfusion fluid are 3-30 mmole/l, again reflecting a fluctuating degree of equilibration. The values for tissue glucose calculated from the perfusate glucose and perfusable sodium contents again are sufficiently close to the blood glucose values obtained simultaneously. Once again, the glucose concentration in the tissue is slightly lower than the concentration of blood glucose. It should be noted that even lower glucose concentrations were measured in the tissue than in the blood at the time of insulin administration through the subcutaneous needle, which — in addition to particularly strong glycolysis in the initial stage — might indicate increased local insulin effects causing glucose absorption in the cells and a corresponding drop of the glucose level outside. For this reason it is recommended for the time being to keep the distance between the perfusion fluid line and the point of insulin release into the tissue as large as possible, or to administer the insulin by means of a second needle at a different site.

I claim:
1. A device for determining the concentration of at least one substance of interest in tissue of a living organism, comprising:
  (a) a subcutaneous needle/catheter insertable into the tissue of a living organism, said subcutaneous needle/catheter defining a tip and first and second passages, said first passage being configured as an exchange channel with first openings in wall areas for communication with said tissue and the second passage being configured as a drainage passage, said exchange channel being in communication with said drainage passage via at least one second opening near said tip of said subcutaneous needle/catheter;
  (b) a feeding/draining unit for feeding perfusion fluid into said exchange channel and draining said perfusion fluid from said drainage passage after said perfusion fluid has contacted said tissue via said first openings and become partially balanced by said at least one substance of interest in said tissue,
  (c) an analyzing unit connected to said drainage passage for analyzing said perfusion fluid for said at least one substance of interest, and including means for analyzing endogenous or exogenous marker properties indicative of the degree of interaction between said perfusion fluid and said tissue, and
  (d) an evaluation unit connected to said analyzing unit and including means for determining the concentration of said at least one substance of interest using said degree of interaction.

2. A device according to claim 1, wherein said feeding/drainage unit comprises a reservoir for said perfusion fluid, means forming a feeder passage which connects said reservoir with said exchange channel, a pump for circulation of perfusion fluid from said reservoir into said feeder passage, and a collecting vessel for perfusion fluid; wherein said analyzing unit includes sensors; and wherein said device includes a calibrating unit for calibrating said sensors in said analyzing unit, said calibrating unit comprising a container for calibrating solution, a valved connecting passage which connects said container with said analyzing unit, a pump for circulating said calibrating solution into said connecting passage, and a collecting vessel for said calibration solution.

3. A device according to claim 2, wherein said subcutaneous needle/catheter defines a base formed as a plug-in connection and wherein said feeder passage is contained in a plug which is insertable into said plug-in connection to provide communication between said feeder passage and said exchange channel.

4. A device according to claim 1, including a drug delivery unit which comprises a drug container, a drug feeding tube connecting said drug container with said subcutaneous needle/catheter and defining a drug discharge opening for discharging drug into said tissue, and a drug delivery pump for circulating drug from said drug container into said drug feeding tube.

5. A device according to claim 1, wherein said subcutaneous needle/catheter consists of first and second cannulas of respectively larger and smaller diameters, said second cannula being within said first cannula, said exchange channel being formed in an annular area between said first and second cannulas, said inner cannula not extending to said tip of said subcutaneous needle/catheter.

6. A device according to claim 1, wherein said subcutaneous needle/catheter includes a partition which extends along a length of said subcutaneous needle/catheter to provide said exchange channel and said drainage passage.

7. A device according to claim 1, wherein said subcutaneous needle/catheter defines a drug release opening near said top thereof and a third passage configured as a drug feeder tube which communicates with said drug release opening.

8. A device according to claim 1, wherein said subcutaneous needle/catheter consists of an outer cannula and an inner cannula, said exchange channel being formed between said inner cannula and said outer cannula, wherein said inner cannula includes a partition which defines said drainage passage and said drug feeding tube, wherein said first openings are in said outer cannula and said at least one second opening is in said inner cannula so as to communicate said exchange channel and said drainage passage.

9. A device according to claim 2, wherein a negative pressure sensor if provided in one of said drainage passage upstream of said analyzing unit, said drainage passage between said analyzing unit and said collecting vessel for perfusion fluid and said collecting vessel for said perfusion fluid, and wherein a temperature sensor is provided in said analyzing unit.

10. A device according to claim 1, including one of an ionic sensor and a conductivity meter in said analyzing unit for determining said marker variable and which acts as a negative pressure sensor, registering adequate filling of a measuring capillary in said analyzing unit, a signal of said evaluation unit effecting switchover or switch-off of a suction pump for said perfusion fluid, and wherein said device includes one of an acoustical alarm and an optical display means.

11. A device according to claim 1, wherein said analyzing unit for measuring said at least one substance to be analyzed and said endogenous or exogenous marker variables is configured as a replaceable unit, and including shutting means to close said passages connected to said analyzing unit upon disconnection of said replaceable unit from said subcutaneous needle/catheter.

* * * * *